(12) United States Patent
Nakamura et al.

(10) Patent No.: US 8,206,928 B2
(45) Date of Patent: Jun. 26, 2012

(54) METHOD FOR DETERMINATION OF PRESENCE OF CROSSING WITH CULTIVATED ROSE IN WILD ROSE

(75) Inventors: Noriko Nakamura, Mishima-gun (JP); Masako Mizutani, Mishima-gun (JP); Yoshikazu Tanaka, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 295 days.

(21) Appl. No.: 12/532,246

(22) PCT Filed: Mar. 21, 2008

(86) PCT No.: PCT/JP2008/056000
§ 371 (c)(1), (2), (4) Date: Sep. 21, 2009

(87) PCT Pub. No.: WO2008/117860
PCT Pub. Date: Oct. 2, 2008

(65) Prior Publication Data
US 2010/0143914 A1 Jun. 10, 2010

(30) Foreign Application Priority Data
Mar. 23, 2007 (JP) ................................. 2007-077882

(51) Int. Cl.
*C12Q 1/68* (2006.01)
*C12P 19/34* (2006.01)

(52) U.S. Cl. ...................................... 435/6.12; 435/91.2
(58) Field of Classification Search .................. 435/6.12, 435/91.2; 536/24.33
See application file for complete search history.

(56) References Cited

U.S. PATENT DOCUMENTS
5,948,955 A * 9/1999 Holton et al. ................. 800/298

FOREIGN PATENT DOCUMENTS
| JP | 2004 275048 | 10/2004 |
| JP | 2006-149202 | 6/2006 |
| WO | 03/097869 | 11/2003 |
| WO | 2004/070036 | 8/2004 |
| WO | WO 2004/070036 | 8/2004 |

OTHER PUBLICATIONS

Supplementary European Search Report dated May 26, 2010 from European Patent Application No. 08722920.9.
Oono, Y et al., "Effects of the Over-Expression of the ro1C Gene on Leaf Development in Transgenic Periclinal Chimeric Plants," Plant and Cell Physiology, Japanese Society of Plant Physiologists, JP, vol. 34, No. 5, Jan. 1, 1993, pp. 745-752, XP008117668.
Noriko Nakamura et al., "The crossing between the cultivated roses and the wild roses under the natural environment," Mar. 24, 2007, vol. 6, p. 506, P211, Horticultural Research (English-language translation).
D.W. Pallett et al., "Within-population variation in hybridisation and transgene transfer between wild *Brassica rapa* and *Brassica napus* in the UK," Annals of Applied Biology, 2006, pp. 147-155, vol. 148, No. 2, London Biochemical Society, London, England.
Zhi Ping Song et al., "Gene flow from cultivated rice to the wild species *Oryza rufipogon* under experimental field conditions," New Phytologist, 2003, pp. 657-665, vol. 157 (3).
B. Desplanque et al., "Genetic diversity and gene flow between wild, cultivated and weedy forms of *Beta vulgaris* L. (Chenopodiaceae), assessed by RFLP and microsatellite markers," Theoretical and Applied Genetics, 1999, pp. 1194-1201, vol. 98 (8), Springer, Berlin & New York.
J.J. Luby et al., "Gene flow from cultivated to wild raspberries in Scotland: developing a basis for risk assessment for testing and deployment of transgenic cultivars," Theoretical and Applied Genetics, 1995, pp. 1133-1137, vol. 90 (7/8), Springer, Berlin & New York.
Noriko Nakamura et al., "The crossing between the cultivated roses and the wild roses under the natural environment," Mar. 24, 2007, vol. 6, p. 506, P211, Horticultural Research (in the Japanese language).
International Search Report issued on Jun. 10, 2008 in International PCT Application No. PCT/JP2008/056000 filed Mar. 21, 2008.
Debner et al., "Use of diploid self incompatible rose genotypes as a tool for gene flow analyses in roses, " Plant Breeding 122, pp. 285-287 (2003).
Debener, T., "The probability of outcrosses between cultivated and wild roses," available at http://www.gmo-safety.eu/en/safety_science/27.docu.html, (extracted May 26, 2006).
Tanaka, Y., "Flower colour and cytochromes P450," Phytochem Rev. vol. 5, pp. 283-291 (2006).

* cited by examiner

*Primary Examiner* — Kenneth R. Horlick
(74) *Attorney, Agent, or Firm* — Drinker Biddle & Reath LLP

(57) ABSTRACT

Disclosed is a method for determining whether or not a wild rose of interest is crossed with a cultivated rose. The method comprises the steps of: examining whether or not a KSN gene containing a transposon (an indicator) is contained in the rose of interest; and determining that the rose of interest is crossed with a cultivated rose when the individual has the transposon-containing KSN gene.

10 Claims, 1 Drawing Sheet

DETECTION OF THE KSN GENE BY A PCR METHOD

METHOD FOR DETERMINATION OF PRESENCE OF CROSSING WITH CULTIVATED ROSE IN WILD ROSE

CROSS REFERENCE TO RELATED APPLICATIONS

This application is the National Stage of International Application No. PCT/JP2008/056000 filed Mar. 21, 2008, and claims benefit of Japanese Patent Application No. 2007-077882 filed Mar. 23, 2007, both of which are herein incorporated by reference in their entirety.

FIELD OF THE INVENTION

The present invention relates to a method for determining the presence of crossing with a cultivated rose in a wild rose.

BACKGROUND ART

Since flowers having new traits are always favored in the flower industry, the development of such flowering plants is industrially important. Breed improvement based mainly on crossing has produced species with a variety of traits. However, in the crossing-based breed improvement, available gene resources are restricted to crossable closely-related plants, and thus colors and traits that can be introduced are limited in most cases, and besides it is rare that single plant species have various colors and traits. In terms of color for example, it was impossible to produce blue roses and carnations, yellow morning glories or geraniums by the crossing-based breed improvement.

However, the use of the gene recombinant technology can realize the development of a variety of traits by introducing various genes into any plants transcending the species barrier and by artificially altering plant metabolisms etc. For example, there is an example wherein in roses and carnations that cannot produce delphinidin in the flower petal, the gene of the flavonoid 3',5'-hydroxylase enzyme that is required to synthesize delphinidin was expressed to produce delphinidin, which enabled the creation of blue flowers that are not present in nature (Tanaka 2006).

However, in Japan, the research and development, cultivation, distribution etc. of such artificially-created gene recombinant plants are required to abide by the regulations set forth in "Law Concerning the Conservation and Sustainable Use of Biological Diversity through Regulations on the Use of Living Modified Organisms" (Cartagena Protocol). In other countries as well, field cultivation etc. of gene recombinant plants have been regulated based on similar laws. Specifically, for plants whose pollens are fertile and for which a horde of crossable closely-related plants occur in Japan, evaluation on crossability, or on the possibility of gene proliferation from a recombinant plant to a closely-related wild species, is obligatory.

In the case of roses for which a horde of closely-related species occur in Japan and which are multiflorous and fructiferous, quantities to be analyzed on the presence of crossing between cultivated and wild species become enormous, and thus the establishment of simple and accurate analytical technologies is being sought after. So far, the one that utilizes microsatellites as the molecular marker has been reported (Debener 2003, 2006). Furthermore, analysis may also be carried out with an identification method based on ploidy determination using flow cytometry. However, any of the above methods had problems that they lacked accuracy, versatility and/or simplicity. Furthermore, since cultivated roses today were created by artificially crossing about 8 wild species, it was not easy to obtain DNA markers that can distinguish cultivated species from wild species.

In accordance with the present invention, the KSN gene, a target gene, is a gene involved in the perpetual blooming of roses obtained from *Rosa chinensis spontanea*, and the gene was created by inserting an about 9 kb transposon into the KSN gene of a one season flowering rose. It is reported that the insertion of a transposon serves to inhibit the expression of said gene, which led to the deregulation of anthogenesis control at the shoot apex promoting anthogenesis, which resulted in the perpetual blooming nature (Iwata et al., Japanese Unexamined Patent Publication (Kokai) No. 2006-149202).

It is already elucidated that roses of the cultivated species contain, in the homologous configuration, said gene having a transposon inserted therein. On the other hand, roses of the wild species have, in the homologous configuration, a KSN gene which, in principle, does not contain a transposon.

As used herein, *Rosa chinensis* is one of the wild species that became an ancestor of cultivated roses, and a one season flowering rose. *R. chinensis spontanea* is a mutant lineage thereof and a perpetual blooming rose.

Patent document 1: Japanese Unexamined Patent Publication (Kokai) No. 2006-149202.

DISCLOSURE OF THE INVENTION

Methods of determining the presence of crossing with cultivated roses in wild roses have been reported, but they lacked versatility. Other methods may be conceivable, but they lacked simplicity and accuracy. Thus, there is a need for a method that can resolve these problems and can determine whether wild roses are crossed with cultivated roses for plants which are fructiferous and for which a horde of closely-related wild species occur.

In cases where an enormous number of individual plants are to be determined for the presence of crossing in order to examine the possibility of gene proliferation of recombinant plants, a method that permits an easy determination of whether a wild rose is crossed with a rose transformant as a pollen parent is specifically required. Thus, the present invention aims to provide a method that permits an easy determination of whether a wild rose of interest is crossed with the pollen of a rose transformant.

After intensive and extensive research in order to attain the above objective, the present inventors have conceived the idea that in a wild rose, a KSN gene containing a transposon can only be detected when the wild rose crossed with a cultivated rose, and have found that using a KSN gene containing a transposon as the indicator, the above objective can be attained, and thereby have completed the present invention.

Thus, the present invention provides a method for determining whether or not a wild rose of interest is crossed with a cultivated rose, said method comprising the steps of: examining whether or not a KSN gene containing a transposon (an indicator) is contained in the rose of interest; and determining that the rose of interest is crossed with a cultivated rose when the individual has the transposon-containing KSN gene.

Normally, in the crossing of a cultivated rose with a wild species in a study for evaluating the effect of transgenic plants on biological diversity, the scattering of pollens of cultivated species resulting in the crossing with wild species in the neighborhood poses problems. Thus, in the method of the present invention, typically the seed parent is a wild rose and the pollen parent is a cultivated rose. Also, typically the above cultivated rose is a rose transformant having a gene introduced therein, in which the gene may be a gene related to color such as the gene of the flavonoid 3',5'-hycroxylase enzyme derived from pansy of the family Violaceae.

BEST MODE FOR CARRYING OUT THE INVENTION

Cultivated-species and Wild Species

Figure 1:
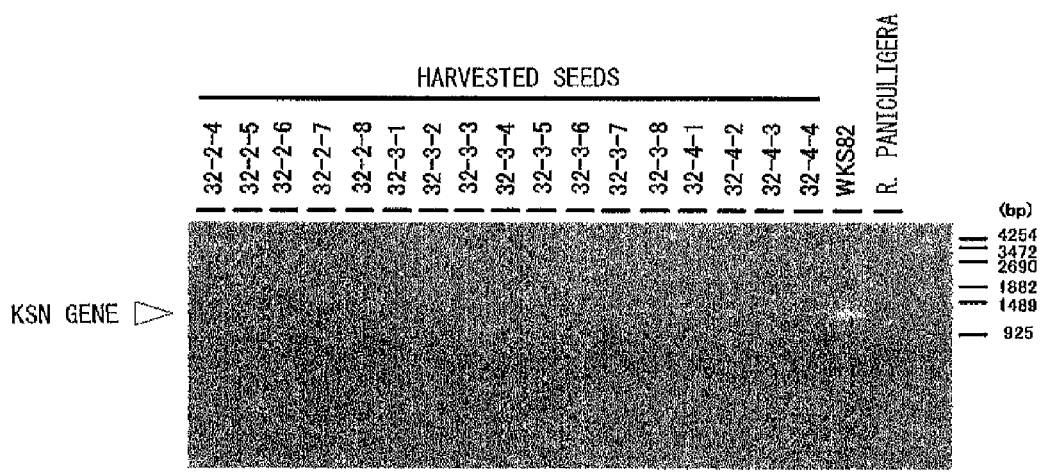
FIG. 1 shows the result of detection of the KSN gene by a PCR method. The position of the specific amplified products of the KSN gene containing introns and the GAPDH gene (internal control) are shown by arrows.
Figure 1:
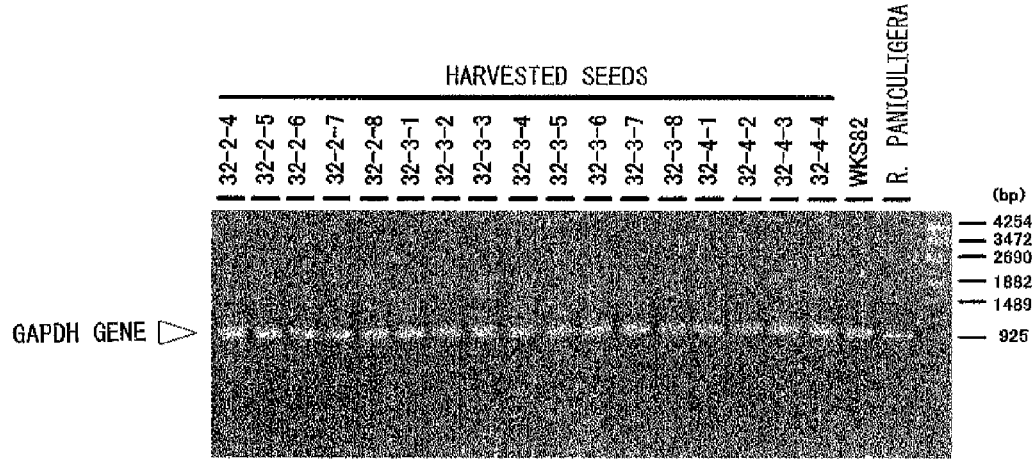

Generally, cultivated roses are tetraploid (4×) and perpetual blooming. In contrast, wild roses are generally diploid (2×) and one-season blooming.

Cultivated roses may be classified into hybrid tea, floribunda and miniature, and all contain, in the homologous configuration, a KSN gene having a transposon inserted therein. Thus, cultivated roses as used herein denote roses that contain, in the homologous configuration, a KSN gene having a transposon inserted therein.

On the other hand, wild roses native to Japan include NOIBARA (*R. multiflora* Thunb. ex Murray), TERIHANOIBARA (*R. wichuraiana* Crep.), HAMANASU (*R. rugosa* Thunb. ex Murray), OOTAKANEBARA (*R. acicularis* Lindl.), KARAFUTOIBARA (*R. marretii* Lev.), OOFUJIIBARA, AZUMAIBARA, YAMATERIHANOIBARA (*R. luciae* Franch. et Rochebr.), YAMAIBARA (*R. sambucina* Koidz.), KAKAYANBARA, YAEYAMANOIBARA (*R. bracteata* Wendl.), NANIWAIBARA (*R. laevigata* Michx.), SANSHOUBARA (*R. roxburghii* Tratt. var. *hirtula* (Regel) Rehd. et Wils.), TAKANEBARA (*R. acicularis* var. *nipponensis* (Crép.) Koehne.), TSUKUSHIIBARA (*R. multiflora* var. *adenochaeta* (Koidz.) Makino), MORIIBARA (*R. luciae* var. *hakonensis* Franch. et Say.), FUJIIBARA (*R. luciae* var. *fujisanensis* Makino), YABUIBARA, NIOIIBARA (*R. luciae* var. *onoei* (Makino) Momiyama), MIYAKOIBARA (*R. luciae* var. *paniculgera* (Makino) Momiyama) and usually have, in the homologous configuration, a KSN gene having no transposon inserted therein. Thus, wild roses as used herein denote rose plants that have, in the homologous configuration, a KSN gene having no transposon inserted therein.

Indicator Gene

In accordance with the method of the present invention, preferably the indicator gene is such that:

(1) the indicator gene is always present in cultivated roses and not in native wild roses.

(2) Cultivated roses are tetraploid (4×), and an indicator gene for crossing must be present in at least three of the four homologous chromosomes, and may preferably be present in all of the four homologous chromosomes. Cultivated roses are tetraploid (4×), whereas native wild roses are diploid (2×). Thus, gametoes produced from cultivated roses may usually be 2×, wild roses may be x, and hybrids produced from the crossing of them may become triploid (3×). Based on this, it is imperative that the indicator gene for crossing be present in at least three of the homologous genes of the cultivated roses. Considering the possibility that a haploid (x) gameto may be produced by heterogenous meiosis from cultivated roses, however, it is preferred, for accurate determination, that the indicator gene is present in all of the four homologous chromosomes.

(3) The same sequence as the partial sequence of the base sequence of the indicator gene is not present in the other regions of the chromosome.

In order to determine the presence of an indicator gene in the plant of interest, said gene must usually be amplified. For this purpose, it is convenient to use a PCR method using a pair of primers that are homologous to the region of the target gene. In this case, when a sequence that hybridizes with said primer is present in other than the target gene, a result that indicates the presence of the gene may be obtained, even if the native target gene is absent. Thus, this requirement is important in connection with primer designing.

Specific Indicator Gene

As a gene that satisfies the above requirement, there can be mentioned a KSN gene having a transposon inserted therein. The KSN gene that is reported as a gene related to the perpetual blooming property of roses (Japanese Unexamined Patent Publication (Kokai) No. 2006-149202) has been demonstrated that it exists as a complete gene encoding 519 amino acids in the wild species whereas in the cultivated-species an about 9 kb transposon has been inserted in the intron segment. Thus, since this transposon is not present in the wild species but present in the cultivated-species, a KSN gene containing this transposon satisfies the requirement set forth in the above (1).

Also, the KSN gene containing this transposon is present in all the four genes of cultivated roses. Thus, this gene satisfies the requirement set forth in the above (2).

The KSN gene containing this transposon also satisfies the requirement set forth in the above (3) by primer selection.

Primers and Probes

The base sequence of the KSN gene (SEQ ID NO: 1) (encoded protein disclosed as SEQ ID NO: 7) and that of a transposon (SEQ ID NO: 2) inserted therein are already known. The KSN gene having this transposon inserted therein is specifically present only in the cultivated roses. In order to detect the KSN gene having this transposon inserted therein by PCR, it is necessary to use, as a pair, a primer having a sequence identical or substantially homologous to the sequence set forth in SEQ ID NO: 1 and a primer having a sequence identical or substantially homologous to the sequence set forth in SEQ ID NO: 2. Furthermore, general conditions as the primer must be met, and any of the primers are an oligonucleotide with a size of 10 bases or more, preferably 15 bases or more, and 50 bases or less, preferably 30 bases or less.

From the purpose of the present invention, it is not preferred that both of the primer pair hybridize with region other than said transposon, though the region to be amplified in the transposon is not specifically limited. As an example of a primer pair that satisfies such requirements, there can be mentioned a forward primer: CATATTATGGCATAGGGTGTGGC (SEQ ID NO: 3) and a reverse primer: TGTAATCTGTAGGAGATCCCATGC (SEQ ID NO: 4).

Detection of the Indicator Gene

DNA extraction from roses, amplification by PCR etc., and the detection of amplified products may be carried out according to standard methods.

Examples

Hereinbelow, details of the present invention will be explained with reference to examples. Unless otherwise specified, molecular biological methods used are based on Molecular Cloning (Cold Spring Harbor Laboratory Press, 2001), Plant Physiol. (2003) 132, 1652-1663.

Reference Example 1

Acquisition of a Gene Specific to a Cultivated Rose by the Random Amplified Polymorphic DNA (RAPD) Analysis In order to determine the presence of crossing with a cultivated rose in a wild rose, the detection of gene polymorphism by the RAPD analysis was used in an attempt to obtain a gene that is specifically present only in the cultivated rose. From each leaf of a wild species (*R. paniculigera*) and a cultivated-species (lavande and WKS82), genomic DNA was extracted using the DNeasy Plant Mini Kit (QIAGEN) according to a method recommended by the manufacturer. A PCR reaction comprising 10 ng of the extracted genomic DNA, 2 μM of any primer (BEX's Common's primer set, CMN-A00), 0.4 mM of a dNTP mixture, 1×Ex Taq buffer, and 0.05 U of Takara Ex Taq was prepared.

The reaction comprised, after reacting at 94° C. for 5 minutes, 25 cycles of 94° C. for 1 minute, 55° C. for 1 minute and 72° C. for 2 minutes, and finally reacted at 72° C. for 7 minutes. The PCR product obtained was subjected to a 0.8% agarose gel electrophoresis to compare the electrophoretic pattern between the wild species and the cultivated-species. The bands that were specifically detected in the cultivated-species were excised from the agarose gel, and purified by the GENECLEAN Turbo Kit (Funakoshi K.K.) according to a method recommended by the manufacturer. Finally, they were subcloned by the pCR2.1 TOPO vector (INVITROGEN) according to a method recommended by the manufacturer, and were subjected to sequence analysis to determine the sequence.

The sequence of each amplified fragment was analyzed. Oligo primers of about 20mer containing a common primer sequence present on both ends of each fragment were created, and the combinations of oligo primers for which amplified products are specifically detected only in the cultivated-species (lavande, WKS82) were examined. With 10 ng of each genomic DNA of *R. paniculigera*, lavande, and WKS82 as the template, a PCR reaction comprising 2 μM of each oligo primer, 1×dNTP mixture, and 0.05 μM of Ex Taq buffer was prepared. The reaction comprised, after reacting at 94° C. for 5 minutes, 25 cycles of 94° C. for 1 minute, 55° C. for 1 minute and 72° C. for 2 minutes, and finally reacted at 72° C. for 7 minutes. The PCR products obtained were subjected to a 0.8% agarose gel electrophoresis to compare the combinations of oligo primers for which amplified products are specifically detected only in the cultivated-species were examined. As a result, the combinations of oligo primers that are thought to provide bands only in the cultivated-species were selected, and subjected to an experiment shown in the following Reference Example 2.

Reference Example 2

Determination of the Presence of Crossing in the Progeny with the Detection of a Specific Gene as an Indicator For plants obtained by artificially pollinating the pollen of a cultivated rose to a wild rose, the presence of crossing was determined using as an indicator the detection of a gene specific to the combination of oligo primers thought to be cultivated-species specific obtained in Reference Example 1.

From the leaf of each progeny obtained, genomic DNA was extracted using the DNeasy Plant Mini Kit (QIAGEN) according to a method recommended by the manufacturer.

Then using this as the template, 2 μM of the primer, 0.4 mMi of a dNTP mixture, 1×Ex Taq buffer and 0.05 U of Ex Taq were subjected to the reaction. The reaction comprised, after reacting at 94° C. for 5 minutes, 25 cycles of 94° C. for 1 minute, 55° C. for 1 minute and 72° C. for 2 minutes, and finally reacted at 72° C. for 7 minutes. The PCR product obtained was subjected to a 0.8% agarose gel electrophoresis to confirm the detection of specific bands. However, though the individual plant morphology apparently exhibited an intermediate trait, no correlation with the presence of specific bands was obtained. This suggested that the RAPD marker obtained here may not be the one contained in all of the four homologous chromosomes, but may be derived from a gene sequence present only on some of the four homologous chromosomes of the cultivated-species. Thus, it was determined to be inappropriate as an indicator for the presence of crossing.

Working Example 1

Determination of the Presence of Crossing in the Progeny with the Detection of the KSN Gene as an Indicator The pollen of a cultivated rose was pollinated to a wild rose, and for the plant obtained, the presence of crossing was determined using as an indicator the detection of the KSN gene (WO2004/070036) containing a transposon that is known to be specifically detected in perpetual blooming roses. A plus strand primer on this gene and a reverse strand primer on the inserted transposon were designed and prepared so as to enable the determination of the presence of insertion of a transposon.

From the leaf of each progeny obtained by artificial crossing, genomic DNA was extracted using the DNeasy Plant Mini Kit (QIAGEN) according to a method recommended by the manufacturer. Using this as the template, a total of 2.5 ml of a reaction solution comprising 0.2 μM each of a forward primer KSN1F3: 5'-CAT ATT ATG GCA TAG GGT GTG GC-3' (SEQ ID NO: 3) and a reverse primer KSN1 nsR3: 5'-TGT AAT CTG TAG GAG ATC CCA TGC-5' (SEQ ID NO: 4), 0.2 mM of a dNTP mixture, 1×Ex Taq buffer, and 0.625 U of Ex Taq was prepared and was subjected to reaction. The reaction comprised, after reacting at 94° C. for 5 minutes, 25 cycles of 94° C. for 1 minute, 55° C. for 1 minute and 72° C. for 2 minutes, and finally reacted at 72° C. for 7 minutes. The PCR product obtained was subjected to a 0.8% agarose gel electrophoresis to confirm the detection of a specific band of about 1.2 kb. Also, it was confirmed that the morphology of the individual plant obtained exhibited an intermediate trait of those of the cultivated species and the wild species.

Thus, for the involve plants that can be determined from the morphology to be a cross of the cultivated-species and the wild species, the presence of the transposon-containing KSN gene was confirmed. Based on this, it was determined that individual plants that have no transposon-containing KSN gene are not a cross of the cultivated-species and the wild species. Considering this characteristic, it was indicated that when a species having no transposon-containing KSN gene was used as the distaff side, the identity of cross can be determined by confirming the presence of a transposon-containing KSN gene in the progeny individual plant.

Working Example 2

Determination of the Presence of a KSN Gene in Wild Roses

For the purpose of determining whether a wild rose could be a subject for the determination method of the present invention, the presence of a transposon-containing KSN gene in each wild rose was evaluated. As wild roses, NOIBARA (*R. multiflora* Thunb. ex Murray), TERIHANOIBARA (*R. wichuraiana* Crep.), HAMANASU (*R. rugosa* Thunb. ex Murray), OOTAKANEBARA (*R. acicularis* Lindl.), KARAFUTOIBARA (*R. marretii* Lev.), OOFUJIIBARA, AZUMAIBARA, YAMATERIHANOIBARA (*R. luciae* Franch. et Rochebr.), YAMAIBARA (*R. sambucina* Koidz.), YAEYAMANOIBARA (*R. bracteata* Wendl.), NANIWAIBARA (*R. laevigata* Michx.), SANSHOUBARA (*R. roxburghii* Tratt. var. *hirtula* (Regel) Rehd. et Wils.), TSUKUSHIIBARA (*R. multiflora* var. *adenochaeta* (Koidz.) Makino), MORIIBARA (*R. luciae* var. *hakonensis* Franch. et Say.), FUJIIBARA (*R. luciae* var. *fujisanensis* Makino), YABUIBARA (*R. luciae* var. *onoei* (Makino) Momiyama), MIYAKOIBARA (*R. luciae* var. *paniculgera* (Makino) Momiyama) were used to determine the presence of a transposon-containing KSN gene (WO2004/070036) according to a method described in Working Example 1.

As a result, no specific amplified product (predicted amplified size: about 1.2 kb) of the transposon-containing KSN gene was detected from any of wild roses. On the other hand, the amplified product of the GAPDH gene that served as the internal control was detected in all the wild species. Thus, in these wild roses, the presence of a transposon-containing KSN gene was not recognized.

From the foregoing, it was determined that the method of the present invention that uses a transposon-containing KSN gene as the indicator can favorably use a wild rose as a test subject.

Working Example 3

Validation of the Presence of Crossing with a Cultivated Rose in the Progeny Obtained by Artificial Crossing For a progeny individual for which the seed parent is a wild rose and the pollen parent is a cultivated rose, the presence of crossing was evaluated using the determination method of the present invention.

According to a standard method, immediately before flowering of a wild species, emasculation and bagging were carried out, and when the stamen reached full maturity, the pollens of the host (WKS82) and a transformant (WKS82/130-4-1 and WKS82/130-9-1) were attached in the morning of a fine day. Then, bagging was carried out again to prevent the attachment of other pollens, and the presence of seed formation was examined. The pollen used was obtained by recovering the anther before cleavage, which was allowed to stand in a desiccator having silica gel, and then to obtain the fresh pollen from the anther that cleaved the next day.

As the mother plant for crossing, the wild species used were *R. multiflora* Thunb. ex Murray, *R. wichuraiana* Crép., and *R. rugosa* Thunb. ex Murray.

The presence of seed formation was confirmed for the fruit for which no physiological fruit drop was noted but fruit set was noted at the time point of more than 2 months after crossing. Furthermore, the seeds obtained were recovered, and after a chilling treatment at 4° C. for 3 months, they were sown. In order to confirm the presence of crossing with the host or the transformant and the presence of transmission of the transgene in them, a PCR method was performed according to a method described in Working Example 1 for analysis.

When the seeds were subjected to a chilling treatment, budding, which is usually observed in about one month, was not observed even after the passage of 3 months. Thus, a portion of the sown seeds that did not bud was recovered again, and was sown for a similar analysis. From the seeds recovered again, genomic DNA was extracted using the Nucleon PHYTOPURE for PLANT DNA EXTRACTION KIT (Amersham Biosciences) according to a method recommended by the manufacturer. Furthermore, after amplifying this by the REPLI-g Midi Kit (QIAGEN), the presence of crossing with the host or the transformant and the presence of transmission of the introduced gene in them was analyzed by a PCR method using as the indicator the presence of a KSN gene having a transposon inserted therein. As the internal control, glyceraldehyde-3-phosphate dehydrogenase (GAPDH) gene was used.

```
GAPDH gene-specific primer

Rh GAPDH-237F:                           (SEQ ID NO: 5)
5'-TGT CAT CTC TGC CCC AAG TAA GG-3'

Rh GAPDH-724R:                           (SEQ ID NO: 6)
5'-CAA CAT CCT CAT CGG TGT AAC CC-3'
```

The results are shown in Table 1 and Table 2. The rate of fruit set was very low even when either of the host and the recombinant was used as the pollen parent. The seedling obtained was analyzed by a PCR method, in which a transposon-containing KSN gene was detected and crossing of the wild species with the host or the transformant was recognized, but the transgene derived from the transformant was not detected. Furthermore, when the sown seeds that did not bud were recovered again and observed whether they were sound or not, most of them were "empty (no content of seed)" and normal embryos were confirmed only for a fraction of plants. For these, a similar analysis was performed by the PCR method, in which a transposon-containing KSN gene was detected and crossing of the wild species with the host or the transformant was recognized, but the transgene derived from the transformant was not detected. It was thought from this that the transgene was not transmitted to the progeny, because, for example, the transgene was not contained in the pollen cell of the transformant.

Thus, it was thought that even if the transformant was crossed with the wild species (*R. multiflora, R. wichuraiana,* and *R. rugosa*), there is no possibility of the transgene being transmitted to the progeny, because, for example, the transgene was not contained in the pollen cell of the transformant.

For *R. wichuraiana*, no normal embryos were confirmed in any seed.

Thus, by using the determination method of the present invention, the presence of crossing between a wild rose and a cultivated rose can be very easily evaluated. Also when the transgene cannot be transmitted to the progeny, because, for example, the transgene is not contained in the pollen cell of the transformant, generally the analysis of crossing is often difficult. However, by using the determination method of the present invention, the presence of crossing can be easily determined. Thus, first the presence of crossing is determined using the determination method of the present invention and when it is determined to have been crossed, it is possible to estimate whether the transgene is present in the germ cell of the crossing parent by investigating the presence of the transmission of the transgene.

TABLE 1

The rate of fruit set with the wild species (*R. multiflora*, *R. wichuraiana*, *R. rugosa*)
by artificial crossing and the detection rate of the transgene in the budding
individual

| | Host (WKS82) | | | | | Transformant (WKS82/130-4-1) | | | | | |
|---|---|---|---|---|---|---|---|---|---|---|---|
| | No. of fruit set/No. of crossed flowers | Rate of fruit set (%) | No. of total seeds | No. of crossed individuals/ No. of budding | Rate of crossing (%) | No. of fruit set/No. of crossed flowers | Rate of fruit set (%) | No. of total seeds | No. of crossed individuals/ No. of budding | Rate of crossing (%) | No. of individuals for which the transgene was detected/No. of budding | Detection rate of the transgene (%) |
| *R. multiflora* | 18/251 | 7.1 | 27 | 1/2 | 50.0 | 45/256 | 17.6 | 65 | 3/3 | 100.0 | 0/3 | 0.0 |
| *R. wichuraiana* | 23/260 | 8.8 | 44 | 1/1 | 100.0 | 11/260 | 4.2 | 24 | 0/0 | — | — | — |
| *R. rugosa* | 2/74 | 2.7 | 263 | 0/0 | — | 5/79 | 6.3 | 427 | 3/3 | 100.0 | 0/3 | 0.0 |
| | | | | | | Transformant (WKS82/130-9-1) | | | | | |
| *R. multiflora* | 18/251 | 7.1 | 27 | 1/2 | 50.0 | 34/255 | 13.3 | 59 | 1/4 | 25.0 | 0/4 | 0.0 |
| *R. wichuraiana* | 23/260 | 8.8 | 44 | 1/1 | 100.0 | 14/261 | 5.4 | 44 | 0/0 | — | 0/0 | — |
| *R. rugosa* | 2/74 | 2.7 | 263 | 0/0 | — | 4/71 | 5.6 | 283 | 0/0 | — | 0/0 | — |

TABLE 2

The detection rate of the transgene in the seeds obtained by artificial crossing with
the wild species (*R. multiflora*, *R. wichuraiana*, *R. rugosa*)

| | Host (WKS82) | | | Transformant (WKS82/130-4-1) | | | | |
|---|---|---|---|---|---|---|---|---|
| | 1)No. of seeds recovered | 2)No. of seeds crossed/ No. of seeds analyzed | Rate of crossing (%) | 1)No. of seeds recovered | No. of seeds crossed/2)No. of seeds analyzed | Rate of crossing (%) | No. of seeds in which the transgene was detected/No. of seeds analyzed | Detection rate of the transgene (%) |
| *R. multiflora* | 23 | 11/12 | 91.7 | 58 | 10/10 | 100.0 | 0/10 | 0.0 |
| *R. wichuraiana* | 43 | 0/0 | — | 24 | 0/0 | — | 0/0 | — |
| *R. rugosa* | 257 | 30/33 | 90.9 | 271 | 28/30 | 93.3 | 0/30 | 0.0 |

| | Host (WKS82) | | | | | Transformant (WKS82/130-9-1) | | | | | |
|---|---|---|---|---|---|---|---|---|---|---|---|
| | No. of fruit set/No. of crossed flowers | Rate of fruit set (%) | No. of total seeds | No. of crossed individuals/ No. of budding | Rate of crossing (%) | No. of fruit set/No. of crossed flowers | Rate of fruit set (%) | No. of total seeds | No. of crossed individuals/ No. of budding | Rate of crossing (%) | No. of individuals for which the transgene was detected/No. of budding | Detection rate of the transgene (%) |
| *R. multiflora* | 18/251 | 7.1 | 27 | 1/2 | 50.0 | 34/255 | 13.3 | 59 | 1/4 | 25.0 | 0/4 | 0.0 |
| *R. wichuraiana* | 23/260 | 8.8 | 44 | 1/1 | 100.0 | 14/261 | 5.4 | 44 | 0/0 | — | 0/0 | — |
| *R. rugosa* | 2/74 | 2.7 | 263 | 0/0 | — | 4/71 | 5.6 | 283 | 0/0 | — | 0/0 | — |

*1), 2)Difference in the No. of seeds recovered and the No. of seeds analyzed resulted because empty (no content of seed) seeds, seeds for which DNA extraction was impossible, and seeds for which no amplification of the control gene by PCR was noted were excluded from the subject of the present analysis.

Working Example 4

Validation of the Presence of Crossing Between a Wild Rose and a Cultivated Rose Under Natural Conditions Using the determination method of the present invention, the presence of crossing between a wild rose and a cultivated rose under natural conditions was evaluated.

In the open air, the wild species (*R. multiflora*) was placed at a distance of 1 m and 5 m from the host or the transformant to investigate crossing with the wild species under natural conditions. This study was carried out under a condition in which the host and the transformant and *R. multiflora* were flowering simultaneously. The flowers of *R. multiflora* that were flowering before the start of this study were all removed at the start of this study, and then placed at a predetermined position.

The presence of seed formation was confirmed for the fruit for which no physiological fruit drop was noted but fruit set was noted at the time point of more than 3 months after the completion of the study. Furthermore, the seeds obtained were recovered, and after a chilling treatment at 4° C. for 3 months, they were sown. In order to confirm the presence of crossing with the host or the transformant and the presence of transmission of the transgene in them, a PCR method was carried out according to a method described in Working Example 1 for analysis.

The result is shown in Table 3. For the seedlings obtained from the seeds harvested from any position, no transposon-containing KSN gene was detected or no crossing of the host or the transformant with *R. multiflora* was noted.

This suggested no or very low possibility of crossing of the present transformant with the wild species (*R. multiflora*) under natural conditions.

Thus, by using the determination method of the present invention, the presence of crossing between a wild rose and a cultivated rose could be very easily evaluated. Also when the transgene cannot transmitted to the progeny, because, for example, the transgene is not contained in the pollen cell of the transformant, generally the analysis of crossing is often difficult. However, by using the determination method of the present invention, the presence of crossing can be easily determined, and thus, the presence of transmission of the crossing-transgene could also be easily analyzed.

Working Example 5

Validation of the Presence of Crossing with a Cultivated Rose in the Seeds Harvested from a Native Wild Rose Using the determination method of the present invention, the presence of crossing between a native wild rose with a cultivated rose under normal conditions was evaluated.

According to a method described in Working Example 3, from the seed harvested from a native wild rose, a PCR analysis was conducted using the presence of a KSN gene having transposon inserted therein as the indicator to validate the presence of crossing with a cultivated rose. As the internal control, glyceraldehyde-3-phosphate dehydrogenase (GAPDH) gene was used.

Result and Discussion

The results are shown in FIG. 1 and Table 4.

In the analysis on about 1800 seeds harvested from a total of 17 sites, no specific amplified products (predicted amplified size: about 1.2 kb) of a transposon-containing KSN gene were detected from any of the seeds. On the other hand, the GAPDH gene that served as the internal control was detected in all the individuals.

From the foregoing, it was determined that there is no crossing with a cultivated-species in all the seeds harvested from the native wild roses.

TABLE 3

The rate of crossing with a wild species (*R. multiflora*) under natural conditions and the detection rate of the transgene

| | Host (WKS82) | | | | | | | Transformant | | | | | | | |
| --- | --- | --- | --- | --- | --- | --- | --- | --- | --- | --- | --- | --- | --- | --- | --- |
| | Total | | | | The presence of crossing | | | Total | | | | The presence of crossing | | Presence of transgene | |
| Distance | Total No. of flowers bloomed | No. of fruit set | Total No. of seeds | No. of individuals analyzed | No. of crossed individuals | No. of non-crossed individuals | Rate of crossing (%) | Total No. of flowers bloomed | No. of fruit set | Total No. of seeds | No. of individuals analyzed | No. of crossed individuals | No. of non-crossed individuals | Rate of crossing (%) | No. of detected individuals | Rate of detection (%) |
| | | | | | | | | Transformant (WKS82/130-4-1) | | | | | | | | |
| 1 m | 466 | 206 | 1011 | 300 | 0 | 300 | 0.0 | 485 | 117 | 648 | 129 | 0 | 129 | 0.0 | 0 | 0.0 |
| 5 m | 484 | 145 | 751 | 148 | 0 | 148 | 0.0 | 484 | 40 | 199 | 28 | 0 | 28 | 0.0 | 0 | 0.0 |
| | | | | | | | | Transformant (WKS82/130-9-1) | | | | | | | | |
| 1 m | 466 | 206 | 1011 | 300 | 0 | 300 | 0.0 | 484 | 205 | 1067 | 192 | 0 | 192 | 0.0 | 0 | 0.0 |
| 5 m | 484 | 145 | 751 | 148 | 0 | 148 | 0.0 | 485 | 120 | 592 | 158 | 0 | 158 | 0.0 | 0 | 0.0 |

Thus, by using the determination method of the present invention, the presence of crossing between a wild rose and a cultivated rose could be very easily evaluated.

TABLE 4

Result of analysis on the seeds harvested from native wild roses

| Sample No. | Species name | No. of plants flowered | No. of fruit set | No. of analysis | *1)Total No. of seeds | *2)No. of seeds analyzed | The presence of crossing with a cultivated rose | | Rate of crossing with a cultivated-species (%) |
|---|---|---|---|---|---|---|---|---|---|
| | | | | | | | No. of crossed individuals | No. of non-crossed individuals | |
| 1  | R. paniculigera | 30   | 5    | 5   | 23  | 13   | 0 | 13   | 0.0 |
| 2  | R. paniculigera | 50   | 37   | 37  | 227 | 79   | 0 | 79   | 0.0 |
| 3  | R. paniculigera | 10   | 3    | 3   | 15  | 12   | 0 | 12   | 0.0 |
| 4  | R. paniculigera | 5    | 2    | 2   | 20  | 16   | 0 | 16   | 0.0 |
| 5  | R. paniculigera | 100  | 46   | 46  | 270 | 233  | 0 | 233  | 0.0 |
| 6  | R. paniculigera | 10   | 2    | 2   | 3   | 1    | 0 | 1    | 0.0 |
| 7  | R. paniculigera | 20   | 4    | 4   | 27  | 5    | 0 | 5    | 0.0 |
| 8  | R. paniculigera | 300  | 176  | 176 | 695 | 380  | 0 | 380  | 0.0 |
| 9  | R. paniculigera | 100  | 102  | 102 | 428 | 75   | 0 | 75   | 0.0 |
| 10 | R. paniculigera | 10   | 7    | 7   | 40  | 22   | 0 | 22   | 0.0 |
| 11 | R. paniculigera | 300  | 200  | 20  | 169 | 109  | 0 | 109  | 0.0 |
| 12 | R. paniculigera | 50   | 34   | 10  | 100 | 88   | 0 | 88   | 0.0 |
| 13 | R. paniculigera | 50   | 18   | 10  | 67  | 42   | 0 | 42   | 0.0 |
| 14 | R. paniculigera | 40   | 18   | 10  | 80  | 27   | 0 | 27   | 0.0 |
| 15 | R. paniculigera | 100  | 15   | 10  | 86  | 65   | 0 | 65   | 0.0 |
| 16 | R. paniculigera | 5000 | 1000 | 100 | 792 | 600  | 0 | 600  | 0.0 |
| 17 | R. onoei        | 500  | 29   | 29  | 129 | 52   | 0 | 52   | 0.0 |
| —  | —               | 6675 | 1698 | 573 | 3171| 1819 | 0 | 1819 | — |

*1), 2)Difference in the total No. of seeds recovered and the No. of seeds analyzed resulted because empty (no content of seed) seeds, seeds for which DNA extraction was impossible, and seeds for which no amplification of the control gene by PCR was noted were excluded from the subject of the present analysis.

---

The invention claimed is:

1. A method of determining whether or not a wild rose of interest is crossed with a cultivated rose, which comprises detecting whether a seed of the wild rose comprises a KSN gene containing an inserted indicator transposon; and determining whether or not the wild rose is crossed with a cultivated rose, wherein the presence of the KSN gene containing the inserted indicator transposon in the seed of the wild rose indicates a crossing between the wild rose and the cultivated rose, and wherein the absence of the KSN gene containing the inserted indicator transposon in the seed of the wild rose indicates no crossing between the wild rose and the cultivated rose.

2. The method according to claim 1, wherein the cultivated rose comprises a gene related to flower color, wherein the gene related to flower color is the gene of the flavonoid 3',5'-hydroxylase enzyme derived from pansy of the family Violaceae.

3. The method according to claim 1, wherein hybridization is carried out to detect whether the seed of the wild rose comprises the KSN gene containing the inserted indicator transposon.

4. The method according to claim 1, wherein specific amplification by polymerase chain reaction (PCR) is carried out to detect whether the seed of the wild rose comprises the KSN gene containing the inserted indicator transposon.

5. The method according to claim 4, wherein PCR is carried out via a forward primer: CATATTATGGCATAGGGTGTGGC (SEQ ID NO: 3) and a reverse primer: TGTAATCTGTAGGGAGATCCCATGC (SEQ ID NO: 4).

6. The method according to claim 1, wherein the wild rose has, in the homologous configuration, a KSN gene that does not contain the inserted indicator transposon.

7. The method according to claim 1, wherein the wild rose is selected from the group consisting of NOIBARA (*R. multiflora* Thunb. ex Murray), TERIHANOIBARA (*R. wichuraiana* Crep.), HAMANASU (*R. rugosa* Thunb. ex Murray), OOTAKANEBARA (*R. acicularis* Lindl.), KARAFUTOIBARA (*R. marretii* Lev.), OOFUJIIBARA, AZUMAIBARA, YAMATERIHANOIBARA (*R. luciae* Franch. et Rochebr.), YAMAIBARA (*R. sambucina* Koidz.), KAKAYANBARA, YAEYAMANOIBARA (*R. Bracteata* Wendl.), NANIWAIBARA (*R. laevigata* Michx.), SANSHOUBARA (*R.*

*roxburghii* Tratt. var. *hirtula* (Regel) Rehd. et Wils.), TAKANEBARA (*R. acicularis* var. *nipponensis* (Crép.) Koehne.), TSUKUSHIIBARA (*R. multiflora* var. *adenochaeta* (Koidz.) Makino), MORIIBARA (*R. luciae* var. *hakonensis* Franch. et Say.), FUJIIBARA (*R. luciae* var. *fujisanensis* Makino), YABUIBARA, NIOIIBARA (*R. luciae* var. *onoei* (Makino) Momiyama), and MIYAKOIBARA (*R. luciae* var. *paniculgera* (Makino) Momiyama).

8. The method according to claim 1, wherein the cultivated rose has, in the homologous configuration, a KSN gene having the indicator transposon inserted therein.

9. The method according to claim 1, wherein the cultivated rose is a hybrid tea, a floribunda, or a miniature.

10. The method of claim 4, where PCR iscarried using a first primer capable of hybridizing with a region of the base sequence set forth in SEQ ID NO: 1 and a second primer capable of hybridizing with a region of the base sequence set forth in SEQ ID NO: 2.

* * * * *

SEQUENCE LISTING

<160> NUMBER OF SEQ ID NOS: 7

<210> SEQ ID NO 1
<211> LENGTH: 519
<212> TYPE: DNA
<213> ORGANISM: Rosa sp.
<220> FEATURE:
<221> NAME/KEY: CDS
<222> LOCATION: (1)..(516)

<400> SEQUENCE: 1

```
atg gca aga atg tcg gaa cct tta gtt gtt gga aga gtc ata gga gat      48
Met Ala Arg Met Ser Glu Pro Leu Val Val Gly Arg Val Ile Gly Asp
1               5                   10                  15 gtt ctt gat tac ttt acc cca act act aaa atg att gtc act tac agc      96
Val Leu Asp Tyr Phe Thr Pro Thr Thr Lys Met Ile Val Thr Tyr Ser
            20                  25                  30 acc aaa ctc gtc ttc aat gga cat gag ctc ttc cca tct gca gtc acc     144
Thr Lys Leu Val Phe Asn Gly His Glu Leu Phe Pro Ser Ala Val Thr
        35                  40                  45 gcc aaa cct aga gtt gag att caa gga ggc gac atg aga tca ttc ttc     192
Ala Lys Pro Arg Val Glu Ile Gln Gly Gly Asp Met Arg Ser Phe Phe
    50                  55                  60 act ctg gtg atg aca gac cca gat gtt cct ggc cct agt gat cct tat     240
Thr Leu Val Met Thr Asp Pro Asp Val Pro Gly Pro Ser Asp Pro Tyr
65                  70                  75                  80 ttg aag gag cac ctg cac tgg att gtg aca gac att cca ggc acc aca     288
Leu Lys Glu His Leu His Trp Ile Val Thr Asp Ile Pro Gly Thr Thr
                85                  90                  95 gat gtt aca ttt gga aga gag atg gtg agc tac gag atg cca agg cca     336
Asp Val Thr Phe Gly Arg Glu Met Val Ser Tyr Glu Met Pro Arg Pro
```

-continued

```
                         100                 105                 110
aac ata gga atc cac agg ttt gtg ttt gtt ctt ttc aag cag aaa cga      384
Asn Ile Gly Ile His Arg Phe Val Phe Val Leu Phe Lys Gln Lys Arg
            115                 120                 125 agg cag tcg gtg aac cca cct tct tca agg gat cac ttc aac acc cga      432
Arg Gln Ser Val Asn Pro Pro Ser Ser Arg Asp His Phe Asn Thr Arg
    130                 135                 140 agc ttc gca gcc gaa aac gac ctc ggt ctt cct gtt gct gcc gtt tac      480
Ser Phe Ala Ala Glu Asn Asp Leu Gly Leu Pro Val Ala Ala Val Tyr
145                 150                 155                 160 ttc aat gcg cag aga gaa acg gca gca aga aga cgc tag                  519
Phe Asn Ala Gln Arg Glu Thr Ala Ala Arg Arg Arg
                165                 170

<210> SEQ ID NO 2
<211> LENGTH: 8925
<212> TYPE: DNA
<213> ORGANISM: Rosa sp.
<220> FEATURE:
<221> NAME/KEY: modified_base
<222> LOCATION: (3960)..(3960)
<223> OTHER INFORMATION: a, c, t, g, unknown or other
<220> FEATURE:
<221> NAME/KEY: modified_base
<222> LOCATION: (4004)..(4004)
<223> OTHER INFORMATION: a, c, t, g, unknown or other
<220> FEATURE:
<221> NAME/KEY: modified_base
<222> LOCATION: (4009)..(4009)
<223> OTHER INFORMATION: a, c, t, g, unknown or other
<220> FEATURE:
<221> NAME/KEY: modified_base
<222> LOCATION: (4047)..(4047)
<223> OTHER INFORMATION: a, c, t, g, unknown or other
<220> FEATURE:
<221> NAME/KEY: modified_base
<222> LOCATION: (4075)..(4075)
<223> OTHER INFORMATION: a, c, t, g, unknown or other
<220> FEATURE:
<221> NAME/KEY: modified_base
<222> LOCATION: (4077)..(4077)
<223> OTHER INFORMATION: a, c, t, g, unknown or other
<220> FEATURE:
<221> NAME/KEY: modified_base
<222> LOCATION: (4144)..(4144)
<223> OTHER INFORMATION: a, c, t, g, unknown or other
<220> FEATURE:
<221> NAME/KEY: modified_base
<222> LOCATION: (4322)..(4322)
<223> OTHER INFORMATION: a, c, t, g, unknown or other
<220> FEATURE:
<221> NAME/KEY: modified_base
<222> LOCATION: (4369)..(4369)
<223> OTHER INFORMATION: a, c, t, g, unknown or other
<220> FEATURE:
<221> NAME/KEY: modified_base
<222> LOCATION: (4380)..(4380)
<223> OTHER INFORMATION: a, c, t, g, unknown or other
<220> FEATURE:
<221> NAME/KEY: modified_base
<222> LOCATION: (4487)..(4487)
<223> OTHER INFORMATION: a, c, t, g, unknown or other
<220> FEATURE:
<221> NAME/KEY: modified_base
<222> LOCATION: (4587)..(4587)
<223> OTHER INFORMATION: a, c, t, g, unknown or other
<220> FEATURE:
<221> NAME/KEY: modified_base
<222> LOCATION: (4731)..(4731)
<223> OTHER INFORMATION: a, c, t, g, unknown or other
<220> FEATURE:
<221> NAME/KEY: modified_base
<222> LOCATION: (4735)..(4735)
<223> OTHER INFORMATION: a, c, t, g, unknown or other
<220> FEATURE:
```

```
<221> NAME/KEY: modified_base
<222> LOCATION: (4745)..(4745)
<223> OTHER INFORMATION: a, c, t, g, unknown or other
<220> FEATURE:
<221> NAME/KEY: modified_base
<222> LOCATION: (4752)..(4752)
<223> OTHER INFORMATION: a, c, t, g, unknown or other
<220> FEATURE:
<221> NAME/KEY: modified_base
<222> LOCATION: (6446)..(6446)
<223> OTHER INFORMATION: a, c, t, g, unknown or other
<220> FEATURE:
<221> NAME/KEY: modified_base
<222> LOCATION: (6453)..(6453)
<223> OTHER INFORMATION: a, c, t, g, unknown or other
<220> FEATURE:
<221> NAME/KEY: modified_base
<222> LOCATION: (6515)..(6515)
<223> OTHER INFORMATION: a, c, t, g, unknown or other
<220> FEATURE:
<221> NAME/KEY: modified_base
<222> LOCATION: (6598)..(6598)
<223> OTHER INFORMATION: a, c, t, g, unknown or other
<220> FEATURE:
<221> NAME/KEY: modified_base
<222> LOCATION: (6688)..(6688)
<223> OTHER INFORMATION: a, c, t, g, unknown or other
<220> FEATURE:
<221> NAME/KEY: modified_base
<222> LOCATION: (6708)..(6708)
<223> OTHER INFORMATION: a, c, t, g, unknown or other
<220> FEATURE:
<221> NAME/KEY: modified_base
<222> LOCATION: (6711)..(6711)
<223> OTHER INFORMATION: a, c, t, g, unknown or other
<220> FEATURE:
<221> NAME/KEY: modified_base
<222> LOCATION: (6744)..(6744)
<223> OTHER INFORMATION: a, c, t, g, unknown or other
<220> FEATURE:
<221> NAME/KEY: modified_base
<222> LOCATION: (6792)..(6792)
<223> OTHER INFORMATION: a, c, t, g, unknown or other
<220> FEATURE:
<221> NAME/KEY: modified_base
<222> LOCATION: (6794)..(6794)
<223> OTHER INFORMATION: a, c, t, g, unknown or other
<220> FEATURE:
<221> NAME/KEY: modified_base
<222> LOCATION: (7247)..(7247)
<223> OTHER INFORMATION: a, c, t, g, unknown or other
<220> FEATURE:
<221> NAME/KEY: modified_base
<222> LOCATION: (7276)..(7276)
<223> OTHER INFORMATION: a, c, t, g, unknown or other
<220> FEATURE:
<221> NAME/KEY: modified_base
<222> LOCATION: (7442)..(7442)
<223> OTHER INFORMATION: a, c, t, g, unknown or other

<400> SEQUENCE: 2
tgtaagtaca ttggcctatt accattcaac atatgatttc ccactacgac gaggaaaccg      60
gagcttcaag gaagcaaaga gaaagatcac aagatcggtt cttgaagaca agatcaagtc     120
aaatcgagtc actgatcttg agtttaatgt gtattcattc catattggtt ggtataaatc     180
taaattgata tgcatatcgg ttgtattaag tcaataatcc cttatgcatt aaaatggttt     240
ttaacatgca tatcaatttg agaccttgtt aggaaagtat cgattgcaca ttcaaaaact     300
gttttaaatc tttctatatt tatcttaatc aattatcaag aaaagatttg attgagggg      360 agttttctc ccttataaaa aggtttcaaa actaaagttt tgtgtagggt ttttgacggc      420
tgaaactggt ttctctttga acttcttgtt ttgttcaaat cgttttcgaa aaaccctctt     480
taattgtttc atgtattact ttgcataatc ttttacatcc actctcaaga tcagtgattc     540
```

```
aattgagtga aaggaaggct gaagattgat tgcctggaat gttgaatcta gagttagaat    600
ggttgtaaaa caagttagca tttgttgcta agaaaaggtg tttgttgtga acaacactac    660
ttgtattctg taaactctag tgtttaatat tggattgatt tttcgtgttg gctacgttaa    720
aagccacgca gtgaagtttc ctcagtggag aggtttacac tgcgttagca aatcttcgtg    780
tcatgtatca tactttcttt gattaaactc ttgagaaaaa gtattttatc aacactggtt    840
ccatctagta ttttcaattg gcatcagagc gggttctaga accttctaga gatcccagga    900
aagatggaac attcacgtga tagggctact gggggatcta taaatagtcc tccctggttc    960
gaaggtggat gtgaaaaata cactcaatgg aagatttaca tgaaatcata cctctatgct   1020
caagatgaac acgtgtggaa catcgtagaa aatggctgga gtgtacctat gacaaaagca   1080
aaagaagaag gcgcttccac taccactccc aaaccaagga aggactggac tgaggaagaa   1140
gttcgtaact tgcaagcaga tttcaaagcg aagaacagca tcttcacagc cctatcggag   1200
cgggaaaaac tgaggataag tcattgtgag actgccaagc aggcatggga tctcctacag   1260
attacatacg aaggaaataa aaaggtacgt gcacagaaac tgcaagcact gattttgaa    1320
ttcgaaacca tgactatggc agatgatgga accgtggatg acttccatgg tagaattctt   1380
aaaatctccg gtcagtgtcg cagtctagga gcacctttg atgaagataa aatagtcaaa    1440
aagatactca gggctctgcc ggaaaaattt cactcaaagg ttacgagcat agaggactct   1500
tttgatatag atgattatcc acttgatgag ctcatcggaa atttgaaaac ctatgagatg   1560
atgttaaaac ctgagaagaa aaacaagggc gtagccttca aagcagtgaa agaaattgaa   1620
gaggaagaag gatcactaga tcttgctcta ctgacgaagg aattcaaaaa atttctcaaa   1680
agcaagaact cctctaaaaa cacgaatgct cccagaagga ataaccatat tggcagtggt   1740
aacaacagtg actacaatag taagaatgga agaggaaact tcaaaggaaa tcactcaagg   1800
aaaccaaaat gctatgaatg tggtggtttc ggtcacattt ctactgactg tggaaatagg   1860
aagcttggaa acagcaacaa caagtcactc cttcaacttt ggagtgatga tgaatctcaa   1920
gaaattgaaa atgtggctct tgtctcatca ttgttgcctg attctgaaag tgatgagtat   1980
ttctctgatg atgatgaaac aaatgttcgc tgcaaacaac tctacaaagc ttcaaaggcc   2040
actctgatta gaaacttgag cttggaaaaa gaagtagatt tcctgaggac tgaaaaagaa   2100
aaggtggaga aactattcga atcctcacaa tctgcatgga aactggagaa aagcaaactc   2160
gtgagtgaat cggcagatct acaaggtgac caaaagatac tgacgtggaa gactgaaaag   2220
aatgagtatc tcaacaagat caaacttcta gaactggatt taaaggaca aagagccctg    2280
aacttggaac tgttagcgaa aaatgagtct ctacaacatg agttaaaatt aactcaagaa   2340
agattcatga gtttgatat cagctccact tccatgtcca agttacttgg atcaggaaaa    2400
gctcctcatg atacatgtgg gctaggatac actggagaag attccaaaag caccaaattc   2460
gtacgtgcct caaaaccatc tgtagagcag atagatgtct cccttgatga tcatgtcaaa   2520
agtgtaaggg aaggtaattc aaaccaacat catcaggtaa aacttgacca agaatccccc   2580
actggtcaac acaggtacgc aaaccctaga accttgtgtc ctacttgtca tcactgtggt   2640
aagattggcc atatcagacc tagatgtaat gaacggtttt taaacttaca atttctcaa    2700
gaaaaatgta ctgtcgaaac cttacaggtt gagcttaaag aacaaaagga actcattaac   2760
aaattaactg aaattgtttc tcaaaagaat cctcaaactg aagaagaaa agatgtctgg    2820
accagaaaaa ttaaaagcaa aaatcattgg tcccctgttg gtgaaactga tgatacatgt   2880
cttttttgttt gtgctagcaa aattcatcaa cgctctcaca ttgaggcaac ttgtttggta   2940
```

```
gctttaactg catttgctga caaacgacga gatttttggt atgttgacag tggttgttct    3000
agacacatga ctggagacaa aacctggttt acttcatttg aggatgaaaa tacctctgga    3060
tcagtcacgt ttggagatgg gaggaaagct aacattctag ctcgaggtac agtaaacact    3120
ccaggtatac ctaaccttaa aaatgtgtta tttgttgaag gattaactgc aaatctgatt    3180
agcgtcagcc atttggctga tgactatgaa gatgtgtggt ttaacaaaca gagatgtttg    3240
gtcctaaatc agaaaggtga aggtatcatg ggaggtatga gatctgttga taactgttat    3300
catattcaag caaatgaatc ttctagtttg cagtcttgtt tgtctgttaa atccacagag    3360
gaaacctttg aactttggca cagaaagatg ggacatatca actatcagga cttgctgaaa    3420
ttatcttcca acaatgtgt ccgaggcttg ccaaatttaa aaggtaaaac tgacaagatg    3480
tgtggagact gcaaggttgg aaagcaaact aaggcacctc acagaatggt aaattctgcg    3540
acaacctcac aagtattgga actattacac atggatctca tgggaccagc tcaatctgaa    3600
agtcttggag gtaagagcta catactagta gttgtagatg atttctcaag atacacctgg    3660
gtaaacttct tgaaagacaa aactgaaacg tttgagtcct ttaagaactt gagtcaaaaa    3720
ttaatcattg agaacaatc atctaataac tgtttagtga gaataagatc agataatgga    3780 actgagtttta aaaatgcctc ttttttctaac tactgtcatg agcttggtgt gtcacatgag    3840
ttctcagctc aataacccc tcaacaaaat gggatagtgg aaaggaaaaa tagggtactg    3900
ctagacatgg ctcgagtatt actacacgct gcaggtttaa gcaaaaactt tgggctgan    3960 gcgatcagca ctgcttgcta cacaataaat agagtattcc ttanaccang aaatgatcaa    4020
actgcttacg agctgtggaa aggtaanaag ccaaatgtta aacactttca tgttntnggc    4080
agtccttgtt acattctacg agatagaaa caccttggta agtttgatgc tagaactgat    4140
gatngtgtgt tcttggggta ttctctgaac agcagagcat atagggttta caataaaaga    4200
actcgtgttg ttatggaatc cattaatgtt tctattgatg atcaatgtgt gaaacaggaa    4260
gtaacatttg cagatacctc acccttctcg gtcacacctt cacagaatac tgaaacatca    4320
tntgaggaag aggaagagga aatccatgac aacatttttg aaccagctnc cacccaaagn    4380
agagggttca gcaagttca aaaagatcac tccactcaag atatcatcgg caatctaaca    4440
gatggtccga tgacaaggag aaaggctgca gttcaggtaa gtccctntga ggtaagtgaa    4500
ggaaatgtat tactgtgttt cattaccgaa aatttggtaa gcatgaacat tatatctcat    4560
tttggttttg tgtccattat tgaaccnaaa aatattaagg cagccttgtt ggatgataac    4620
tggattagcg ccatgcaaga tgaactgaat cagtttacta ggaatgatgt atggtactta    4680
gtaccaaggc ctagtaagtg caatgttata ggaactaagt ggattttcag naatnaaagc    4740
gatgntaaag gnaacgtgat taggaataaa gccagactag ttgctcaggg atattcacag    4800
gtcgaaggac ttgactttga cgagactttt gctcctgtag ctaggttgga atctgttaga    4860
ttacttctat ccattgcttg tcatctccgg ttcaaattgt ttcaaatgga tgtcaaaact    4920
gcctttctga atggatttct tcaggaggaa gtttatgtag agcagcctcc aggtttccaa    4980
gatccacaca acctagatca tgtctaccgg ctcaagaaag ccctgtatgg gctaaagcag    5040
gctcctcgag cctggtatga gagactatcc actcatcttg tgggaaaagg gtatgctaga    5100
ggatccatag ataaaacatt gtttgtgaaa cgaaccaaaa atgacattgt cattgcccaa    5160
gtgtatgttg atgatattgt atttggttcc acttctaaat accttgtcaa agaatttcaa    5220
tctgtcatgg aaagtgaatt tgaaatgagc atgtgtggtg aactaacgta ttttcttgga    5280
ctgcaagtaa agcagataga cacaggtttg tttctctctc aatcaaaata cgctgagaac    5340
```

```
ctgatcaaga aattcggtct tgcttccaag aagacagtga ccaatcccat gagtacaact    5400
actaagttaa gcgaagatca tgaaggaaaa tcagttgatc cgactctcta tcgaagtatg    5460
atcgggagtt tgctctatct cactgccagc agacctgaca tctcttacag tgtgggtgtg    5520
tgtgctcgat ttcaagcaaa ccccaaagaa tctcacctgg acgctgtcaa agaataatc     5580 cgctatgtgg caggtacagt taattgtggc cttttctata ccttcgacac taatgtagaa    5640
attgcaggat actctgatgc tgactgggga ggaaatttaa aggatcggaa aagcacttca    5700
gggggatgtt ttttcattgg caacaatctg gttgcctggc atagtaagaa acaaaactgc    5760
atatccttgt ctactgcaga agctgaatat gttgccgctg gaagttgctg cacacaaata    5820
ctttggatga agcaaatgct tcatgattat ggcatatctc aaggtaagtt gtctattttc    5880
tgtgacaaca ctagtgctat taacatcact aagaatcctg ttcaacactc tcgaacaaag    5940
cacattgatc tccgatatca ctttattagg gatttggttg aacaaaacat acttgagtta    6000
agctttgtgc ccactgaaaa tcaacttgct gatctgttca ctaagcctct tgacactgct    6060
aggtttgaaa tgttgaggaa tgccctaggg atatgttcta agcattaagg caaaatgatg    6120
actgtccact attgattgag aaaattgtga tcctagtatc ccttgatcac agtcactagt    6180
gaaatgtaca tattttcagt catgtatctt aatgttatca tgccttattc tggacaaatg    6240
aaattgtgta ctcatgttta gtcactgaat caagtaaccc tactatgcat cttcacctat    6300
agcctatgtg gtggcatgtt tccttttgtt ttctgtcaaa tgagattcag tgaagtagac    6360
gaactgcttc ttttgctcac ataactaatt ccctcttctc aaagtaatca ggtcctagtt    6420
gtggtgaact ttctaggatt tgtaanaaac ganaacggaa aattgtatcc catctctcaa    6480
agtaatcagg ccttagtcgt ggtgaacttt ctaangtttg caagaaacga gctggtgagt    6540
ggtctttgca cataacataa aatcatgcag acaactactc gagactctct ccatgganca    6600
tccttgttat gctagtacc ctaagaacat ctgttctggg ggttgctgag aagagtcttg     6660
ttacatgagt aatatttgtc actaaatnaa ggagatcttt gactccanta nacatgtgct    6720
tgggaccatg attcctgctc cttnttagga gatttcatga gctttacttt agttctctta    6780
cttcactcct tntntatgac actaaaatct tttctaagcc ccacatcatg gttatattca    6840
cttctatcac aagttactc cttaaggtct aactatgagt accaattctt attgttgaga     6900
gaatacatca tgcttcgtac tctgaactat gtgccttcca ctaagtgatc tgtgctctct    6960
gtgattaaac ttcgctatat tttctctcct cgatatgacc tatgcattca ttgccttgat    7020
acttgcaaag gaaacgatcc tctgatatac ttgcagattc tctgaatata ttttggctct    7080
tcgtttcctt ccttgatggt aatctgccta caattaattt ccataatgac tatgcctaag    7140 ttgagggggga gaagttatct gcatgcatat acctagggaa aataaattgt cataacttct    7200
ctccccattt gagccgttct cccaatcggt gtgttccttg gtcttcntaa aacctaactg    7260
ttcactacat atagcntctc ttgtctccct cggattttac tcttggttgt ctctgtgtgc    7320
aggttctttc acccactgct ctctcaccat ggttcgctca cagcaaacaa ctcgccttgg    7380
aggacatcgc cgcctgcctc ctccagaaga aggtcgtcag gcagctgcca gagccgggat    7440
tntccatccc ggcatgcatc gtacacgcag tcggagtcct cctcctcctg tctctctgga    7500
aagtctccgt gatcagattc tagtggctga ctggcgaatt gcttgcctca cgacggacat    7560
ggacgacatg cattctcttc tggttcgaac tcgtcatgcc ctgaccactc tcacacagga    7620
gatccggaac atgcagcgcc accctccgg gtttgacgct cccggtccat cccatgccat     7680
gcaggagcct gtcgcaccag aggaaagctc ggattccatg gatgaagagg aatttctgga    7740
```

-continued

```
caccgtcacc aagctttgtg aggaatttga cgtgccctcc cattcaaagg gggagaagta   7800
acttgatttt tcttacttta tttctgtttc tgcatttta atttttttg gtgtgtaagt     7860 gcataagcac agatactctt aggatgcttg ctattattat tcttaagtaa tcgtattttg   7920
gctacttgga tccggaaaag gatggaaact gattccttac tccaagtagc acccttgtt    7980 tagtgattag tgtttatctg tgaaacctaa cttgcaggac aaaagatgaa aaatcatgcg   8040
ttgaatggga atgcccaaag ggggagattg taagtacatt ggcctattac cattcaacat   8100
atgatttccc actacgacga ggaaaccgga gcttcaagga agcaaagaga aagatcacaa   8160
gatcggttct tgaagacaag atcaagtcaa atcgagtcac tgatcttgag tttaatgtgt   8220
attcattcca tattggttgg tataaatcta aattgatatg catatcggtt gtattaagtc   8280
aataatccct tatgcattaa aatggttttt aacatgcata tcaatttgag accttgttag   8340
gaaagtatcg attgcacatt caaaaactgt tttaaatctt tctatattta tcttaatcaa   8400
ttatcaagaa aagatttgat tgaggggag ttttctccc ttataaaag gtttcaaaac      8460 taaagttttg tgtagggttt ttgacggctg aaactggttt ctctttgaac ttcttgtttt   8520
gttcaaatcg ttttcgaaaa accctcttta attgtttcat gtattacttt gcataatctt   8580
ttacattcac tttcaagatc agtgattcaa ttgagtgaaa ggaaggctga agattgattg   8640
cctggaatgt tgaatctaga gttagaatgg ttgtaaaacc aagttagcat tgttgctaa    8700 gaaaaggtgt ttgttgtgaa caacactact tgtattctgt aaactctagt gtttaatatt   8760
ggattgattt tcgtgttgg ctacgttaaa agccacgcag tgaggtttcc tcagtggaga    8820
ggtttacact gcgttagcaa atcttcgtgt catgtatcat actttctttg attaaactct   8880
tgagaaaaag tattttatca acactggttc catctagtat tttca                   8925
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
catattatgg catagggtgt ggc                                            23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgtaatctgt aggagatccc atgc                                           24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tgtcatctct gccccaagta agg                                            23

```
<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caacatcctc atcggtgtaa ccc                                            23

<210> SEQ ID NO 7
<211> LENGTH: 172
<212> TYPE: PRT
<213> ORGANISM: Rosa sp.

<400> SEQUENCE: 7

Met Ala Arg Met Ser Glu Pro Leu Val Val Gly Arg Val Ile Gly Asp
1               5                   10                  15

Val Leu Asp Tyr Phe Thr Pro Thr Thr Lys Met Ile Val Thr Tyr Ser
            20                  25                  30

Thr Lys Leu Val Phe Asn Gly His Glu Leu Phe Pro Ser Ala Val Thr
        35                  40                  45

Ala Lys Pro Arg Val Glu Ile Gln Gly Gly Asp Met Arg Ser Phe Phe
    50                  55                  60

Thr Leu Val Met Thr Asp Pro Asp Val Pro Gly Pro Ser Asp Pro Tyr
65                  70                  75                  80

Leu Lys Glu His Leu His Trp Ile Val Thr Asp Ile Pro Gly Thr Thr
                85                  90                  95

Asp Val Thr Phe Gly Arg Glu Met Val Ser Tyr Glu Met Pro Arg Pro
            100                 105                 110

Asn Ile Gly Ile His Arg Phe Val Phe Val Leu Phe Lys Gln Lys Arg
        115                 120                 125

Arg Gln Ser Val Asn Pro Pro Ser Ser Arg Asp His Phe Asn Thr Arg
    130                 135                 140

Ser Phe Ala Ala Glu Asn Asp Leu Gly Leu Pro Val Ala Ala Val Tyr
145                 150                 155                 160

Phe Asn Ala Gln Arg Glu Thr Ala Ala Arg Arg Arg
                165                 170
```